United States Patent [19]

Reifschneider

[11] 4,439,430

[45] Mar. 27, 1984

[54] O,O-DIETHYL O-[(P-TERTIARYBUTYLTHIO)PHENYL]-PHOSPHOROTHIOATES AND ITS INSECTICIDAL USE

[75] Inventor: Walter Reifschneider, Walnut Creek, Calif.

[73] Assignee: The Dow Chemical Company, Midland, Mich.

[21] Appl. No.: 307,964

[22] Filed: Oct. 2, 1981

[51] Int. Cl.³ .................... A01N 57/14; C07K 9/165
[52] U.S. Cl. .................................... 424/216; 260/949
[58] Field of Search .................... 260/949; 424/216

[56] References Cited

U.S. PATENT DOCUMENTS

| | | | |
|---|---|---|---|
| 3,042,703 | 7/1962 | Schegak et al. | 260/949 |
| 3,351,682 | 11/1967 | Baker et al. | 260/949 |
| 4,065,558 | 12/1977 | Gordon | 424/216 |

FOREIGN PATENT DOCUMENTS 1183494 12/1964 Fed. Rep. of Germany.

OTHER PUBLICATIONS

Unverified Translation of Japanese Patent 11880/66.

Primary Examiner—Anton H. Sutto
Attorney, Agent, or Firm—S. Preston Jones; Ronald G. Brookens

[57] ABSTRACT

O,O-diethyl O-[-4-(t-butylsulfinyl)phenyl]phosphorothioate is an active insecticide for the kill and control of cucumber beetle larvae.

3 Claims, No Drawings

O,O-DIETHYL O-[(P-TERTIARYBUTYLTHIO)PHENYL]PHOSPHOROTHIOATES AND ITS INSECTICIDAL USE

BACKGROUND OF THE INVENTION

Many phosphate and phosphorothioate esters are known to have pesticidal activity of one kind or another. Various related sulfur-substituted phosphorothioate esters are also known to be active insecticides and miticides. A number of such esters are described in U.S. Pat. No. 3,042,703, West German Pat. No. 1,183,494 and Japanese Pat. No. 11880/66. These patents all disclose esters having the general structural formula

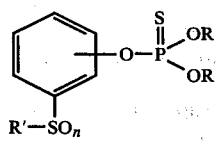

where the phenyl group may have one or more inert substituents, R is a lower alkyl group, usually methyl or ethyl, R' is also a lower alkyl group, and n is zero, one or two. No compounds are shown where R' is a tertiary alkyl group.

SUMMARY OF THE INVENTION

It has now been found that exceptional and different insecticidal activity exists for the compound O,O-diethyl O-[(p-tertiarybutylthio)phenyl]phosphorothioate which corresponds to the formula

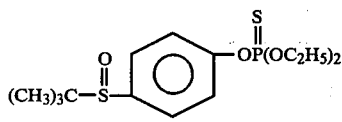

The present invention comprises the above-defined compound, insecticidal formulations containing the compound, and the use of such formulations for killing and controlling the larvae of the western spotted cucumber beetle (*Diabrotica undecimpunctata*).

DETAILED DESCRIPTION

The compound of the present invention is useful in a variety of household, industrial and agricultural operations for the kill and control of western spotted cucumber beetle larvae (*Diabrotica undecimpunctata*).

When applied to their habitat to protect the plants from the attack of these larvae, the subject compound exhibits good residual control of the insect.

The method of the present invention comprises contacting the larvae with an insecticidally effective or inactivating amount of the compound of the present invention. The contacting can be effected by application of the compound to the insect or the soil that constitutes its habitat. The inactivation can be lethal, immediately or with delay, or can be a sublethal one in which the inactivated insect is not able to carry out one or more of its normal life processes. This latter situation prevails when one of the systems of the insect, typically the nervous system, is seriously disturbed.

The inactivation of an insect by the application of an insecticidally effective or inactivating amount of the compound is critical to the method of the present invention. The compound can be employed in unmodified form, or modified by the addition of a pesticidal adjuvant thereto.

Compositions employing the active compound can be in the form of a liquid or a granulated solid; and the adjuvant employed can be any one of a plurality of materials including aromatic solvents, petroleum distillates, water, or other liquid carriers, surface-active dispersing agents, light absorbers, and granular carrier solids. In such compositions, the adjuvant cooperates with the phosphorus compound so as to obtain a composition to facilitate the method of the present invention, and to obtain an improved result. The use of either a surface-active dispersing agent and a granular carrier solid, simultaneously constitute preferred embodiments of the method of the present invention.

The exact concentration of the compound of the present invention in a composition thereof with an adjuvant therefor can vary; it is only necessary that the compound be present in a sufficient amount so as to make possible the application of an insecticidally effective or inactivating dosage. Such a dosage rate is from about 1 to about 100 ppm of dry soil. Generally, for practical applications, the active compound(s) can be broadly applied to western spotted cucumber beetle larvae or their habitat in compositions containing from about 0.00001 percent to about 98 percent by weight of the phosphorus compound(s).

In the preparation of granular solid compositions, the phosphorus compound can be compounded with any of carrier solids such as pyrophyllite, diatomaceous earth, gypsum and the like. In such operations, the granular carrier is mixed with the compound, as active agent or wetted with a solution of the active agent in a volatile organic solvent. Similarly, granular compositions containing the phosphorus product can be compounded with various solid dispersing agents, such as fuller's earth, attapulgite and other clays. These compositions can be employed as treating compositions or can be employed as concentrates and subsequently diluted with additional solid dispersing agent or with pyrophyllite, diatomaceous earth, gypsum and the like to obtain the desired amount of active agent in a treating composition.

Furthermore, the compound, or a concentrate composition containing said compound can be incorporated in intimate mixture with surface-active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the product can be compounded with a suitable water-immiscible organic liquid and surface active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the product or a composition containing the product is applied to the soil to be protected directly in any convenient manner, for example, by means of hand spreaders or sprayers. Application to the soil on a larger scale is conveniently carried out with power spreaders, boom sprayers and fog sprayers. In large-scale operations, granular compositions or low volume sprays can be applied from an airplane. The present invention also comprehends the employment of compositions comprising one or a combination of these phosphorus compounds, an adjuvant, and one or more biologically active materials, such as other insecticides, fungicides, miticides, bactericides, nematocides, and the like.

The (t-butylsulfinyl)phenol which intermediate for making the phosphorothioate ester of the present invention is a known compound preparable by conventional methods.

The O,O-diethyl phosphorochloridothioates reacted with the phenolic reactant to make the ester of this invention is a commercially available material.

EXAMPLE 1

O,O-Diethyl O-(4-(t-butylsulfinyl)phenyl phosphorothioate

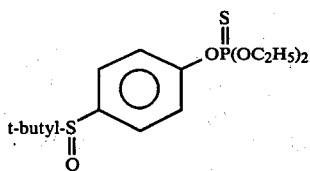

To a stirred mixture of 19.8 grams (0.1 mole) of 4-(t-butylsulfinyl)phenol 150 milliliters of acetonitrile and 16.0 grams of powdered anhydrous potassium carbonate was added 19.8 grams (0.105 mole of O,O-diethyl phosphorochloridothioate. The mixture was heated with stirring at 45°–65° C. for ~4 hours and then left standing, at room temperature, for three days. The reaction mixture was filtered to remove the insoluble salts. The acetonitrile solvent was removed by evaporation under reduced pressure. The residue remaining was dissolved in methylene chloride, washed with 2% aqueous sodium hydroxide and twice with water, and dried over sodium sulfate. After filtration, the methylene chloride was evaporated under reduced pressure to obtain the product as a liquid residue in a yield 85 percent of theoretical and having a refractive index of $n_d^{25} = 1.5365$. Nuclear magnetic resonance spectroscopy confirmed the product to be O,O-diethyl O-(4-(tert-butylsulfinyl)phenyl)phosphorothioate.

For testing the insecticidal activity of the compound, 75 grams of air-dried soil was placed in an 8-ounce container. To the soil was added sufficient volume of a 400 ppm aqueous dispersion prepared by admixing a predetermined amount of the compounds dissolved in acetone with a predetermined amount of water to which some dispersing agent has been added to give various predetermined concentrations of the toxicant in the soil on a soil-chemical basis. The treated soil was air-dried and thoroughly mixed by agitation. To each treated container and to control containers treated with water and the dispersing agent alone, was added 0.5 milliliters of an aqueous suspension of the eggs of the western spotted cucumber beetle (WSCB) (70–80 eggs of 3–4 days old). Additional treated soil was used to cover the eggs and cucumber seed was placed on the soil and covered with additional treated soil. The containers were thereafter maintained under conditions conducive to the growth of the seeds and the hatching of the eggs. Twelve (12) days after treatment, the containers and the plants therein were examined to determine the degree of kill and control of the larvae from the hatched eggs. The results of this examination are set forth below in Table 1.

TABLE 1

| COMPOUND | SOIL CONCENTRATION IN PPM | % KILL OF WSCB LARVAE |
|---|---|---|
| O,O—diethyl O—[4-(t-butylsulfinyl)phenyl] phosphorothioate | 25 | 100 |
| O,O—diethyl O—[4-(n-butylsulfinyl)phenyl] phosphorothioate | 25 | 0 |
|  | 400 | 0 |
| Control | — | 0 |

In each case, it is seen that the tertiary butyl substituted compound of the invention provides complete kill and control of the larvae at a relatively low concentration in the soil whereas the corresponding n-butyl compounds are entirely ineffective even when present at a much higher concentration.

What is claimed is:

1. A method for killing and controlling the larvae of the western spotted cucumber beetle which comprises contacting said larvae or their habitat with a composition containing as an active ingredient an insecticidally effective amount of O,O-diethyl O-[4-(t-butylsulfinyl)phenyl]phosphorothioate in intimate admixture with an inert carrier.

2. The compound O,O-diethyl O-[4-(t-butylsulfinyl)phenyl]phosphorothioate.

3. An insecticidal composition comprising as an active ingredient an insecticidally effective amount of O,O-diethyl O-[4-(t-butylsulfinyl)phenyl]phosphorothioate in intimate admixture with an inert carrier therefor.

* * * * *